United States Patent

Scheuren

(10) Patent No.: US 8,896,831 B2
(45) Date of Patent: Nov. 25, 2014

(54) METHOD AND DEVICE FOR THE VALIDATION OF CONTAMINATION AND CLEANING IN A SYSTEM

(75) Inventor: Hans Scheuren, Regensburg (DE)

(73) Assignee: Krones AG, Neutraubling (DE)

( * ) Notice: Subject to any disclaimer, the term of this patent is extended or adjusted under 35 U.S.C. 154(b) by 258 days.

(21) Appl. No.: 13/446,059

(22) Filed: Apr. 13, 2012

(65) Prior Publication Data

US 2012/0281214 A1    Nov. 8, 2012

(30) Foreign Application Priority Data

Apr. 13, 2011    (DE) .......................... 10 2011 007 309

(51) Int. Cl.
*G01N 15/02*    (2006.01)
*B08B 9/00*    (2006.01)
*G01N 33/02*    (2006.01)

(52) U.S. Cl.
CPC .............. *B08B 9/00* (2013.01); *G01N 15/0205* (2013.01); *G01N 33/02* (2013.01); *G01N 15/0211* (2013.01)
USPC ............................ 356/336; 356/445; 356/436

(58) Field of Classification Search
CPC ....................... G01N 15/0205; G01N 15/0211; G01N 15/1459; G01N 2021/4716; G01N 15/1434; G01N 21/05; G01N 21/15; G01N 21/27; G01N 21/31; G01N 21/85; G01N 33/14; G01N 15/08; G01N 33/02
USPC ......................... 356/336, 445, 436
See application file for complete search history.

(56) References Cited

U.S. PATENT DOCUMENTS

| 4,783,599 | A  | * | 11/1988 | Borden .......................... 250/574 |
| 4,931,660 | A  | * | 6/1990  | Mayer ........................... 250/575 |
| 5,291,626 | A  | * | 3/1994  | Molnar et al. .................... 8/158 |
| 5,710,373 | A  |   | 1/1998  | Osmanski |
| 5,834,642 | A  |   | 11/1998 | Decain et al. |
| 6,290,838 | B1 | * | 9/2001  | Mifsud et al. ................. 205/775 |
| 6,337,739 | B1 | * | 1/2002  | Koelblin et al. .............. 356/336 |
| 6,357,456 | B2 | * | 3/2002  | Segers ......................... 134/25.3 |
| 7,738,101 | B2 | * | 6/2010  | Mavliev ........................ 356/336 |
| 2007/0089489 | A1 | * | 4/2007 | Lewnard et al. .................. 73/38 |
| 2009/0128810 | A1 | * | 5/2009 | Bates ............................ 356/336 |

FOREIGN PATENT DOCUMENTS

| CN | 1699961 A     | 11/2005 |
| DE | 36 15 259 A1  | 11/1987 |
| DE | 102009009426 A1 | 10/2009 |
| EP | 0 310 740 A2  | 4/1989  |
| EP | 2 284 517 A1  | 2/2011  |
| WO | WO-9800694 A2 | 1/1998  |

OTHER PUBLICATIONS

Search Report for German Patent Application No. 10 2011 007 309.4, dated Apr. 4, 2012.
Notification of First Office Action. The State Intellectual Property Office of P.R. China, Application No. 201210111059.9, dated Feb. 19, 2014.

* cited by examiner

*Primary Examiner* — Tarifur Chowdhury
*Assistant Examiner* — Isiaka Akanbi
(74) *Attorney, Agent, or Firm* — Marshall, Gerstein & Borun LLP (57) ABSTRACT

A method for the determination of the degree of contamination of an examination object, such as a system for filling liquid foodstuffs, or a component or subsection of a system, in particular a pipe, including measuring a property distribution of a first examination medium before and after passage through the examination object.

24 Claims, 5 Drawing Sheets

METHOD AND DEVICE FOR THE VALIDATION OF CONTAMINATION AND CLEANING IN A SYSTEM

CROSS-REFERENCE TO RELATED APPLICATION

The present application claims the benefit of priority of German Application No. 102011007309.4, filed Apr. 13, 2011. The entire text of the priority application is incorporated herein by reference in its entirety.

FIELD OF THE DISCLOSURE

The present disclosure relates to is a method for the determination of the degree of contamination of an examination object, such as a system or parts of this system, and furthermore the determination of the cleaning property of the examination object and a device for implementing the method, such for a system of filling liquid foodstuffs.

BACKGROUND

The assessment of a production system or individual subsections or components, in particular pipes, of a system with regard to its contamination tendency and cleanability has been the object of examinations for years. A system of this nature or subsections, components, in particular pipes, in a filling machine are in the following designated as the "examination object". The contamination tendency, that is the degree of contamination, as well as the cleanability, that is the degree of cleaning, of an examination object of this nature can also be abbreviated in the following as the "hygiene status". In general the operation of a system, often also an existing system, is to be supplemented with an individual cleaning management system. For this purpose it is expected that the system can output a message or signal which indicates the requirement for cleaning. The required degree of contamination for this, that is the evaluation quantity to be considered, has so far not been defined. The cleaning stage takes place as a reaction to a message or respectively a signal of this nature. On reaching a desired degree of cleaning, which also represents an evaluation quantity that is not yet defined, the new, respectively the restored state is displayed with an appropriate message and the cleaning process is terminated. Then the production process can be continued.

A simple implementation of a method of this nature would be a visible signal. For example, the indication of the contamination and cleaning could be achieved with the illumination of, for example, a red light (i.e. system contaminated) and appropriately a green light (system cleaned). So far a process of this nature has not yet been implemented. In this respect the following questions arise during examinations: How does a system become contaminated? How does a system clean itself? How can both processes, the contamination and also the cleaning be acquired and standardized? An answer to the first two questions is often very difficult. Here however it may be possible to formulate an optimum of a system in relation to contamination and cleaning properties. For example, a system of this nature may be difficult to contaminate. A system of this nature would exhibit long service periods and correspondingly short cleaning times. The efficiency of a system of this nature would be very high. On the other hand, a system could exhibit short service periods and correspondingly long cleaning times. The economic efficiency of a system of this nature in comparison to the previous system would be very low here, whereby it is self-evident that it must be assumed that both systems have a similar application.

Contaminations of systems outlined above, in particular systems for filling liquid foodstuffs, often include contamination by particles. The question therefore arises to what extent contamination and cleaning of a system can be considered on the basis of particle technologies. DE 10 2009 009426 A1 describes the measurement method and measurement device for the determination of properties of a fluid flow loaded with particles. Here, the velocity of the carrier fluid is calculated and the velocity of a particle or particles in a flowing medium is derived from that using the knowledge of various particle properties, such as density and shape. Appropriately, a flow tube equipped with sensors is used.

WO 98/00694 describes the simulation of the behavior of a certain particle by substitution of this particle by an analogous, comparable and, in particular, measurable particle (which therefore does not correspond particularly to the particle under consideration), whereby certain properties, such as shape or size, correspond to those of the required particle. Here, one or a plurality of certain defined particles are acquired in their movement and accordingly considered in a process, such as the product sterilization or pasteurization. Particularly in this respect, the dwell time of a particle in the system is considered. Here however it must be considered that an analogue particle is involved that is considered in a simulation.

A classical control element with regard to the microbiological analysis of product and rinsing water samples is the microbiological analysis in the foodstuffs industry. For example, a component to be tested can be contaminated with a micro-organism solution, then cleaned, and then detected with an indicator with regard to remaining contamination and evaluated. The method however involves the destruction of the component to be tested, so a complete system cannot be assessed using this method.

Technical processing approaches also attempt to calculate parameters with regard to the material transport of contamination particles from the boundary regions of a pipe. Here, equations for the transport of heat and material are applied. Here, the predictive calculation or the simulation of the cleaning behavior is the objective. A practical examination is however not provided with this approach. Also, a contamination and therefore an associated service period in the system cannot be calculated. The various techniques and methods supply statements on increasing efficiency and on the monitoring of a cleaning process.

However, these techniques and methods are complicated and generally not suitable for acquiring a complete system, in particular with regard to the totality of the contamination and cleaning properties.

SUMMARY OF THE DISCLOSURE

In view of the problems quoted above and in view of the state-of-the-art outlined, one aspect of the present disclosure is producing an evaluation benchmark and an evaluation tool on the basis of particle technologies, which enables an examination object, such as a system or a pipe, to be quantified with regard to see contamination and cleaning properties.

The method according to the disclosure comprises a method for the determination of the degree of contamination of an examination object, such as say a system, in particular a system for filling liquid foodstuffs, or a component or subsection of a system, in particular a pipe whereby a property distribution of a first examination medium is measured before and after passing through the examination object. In this respect a property distribution is taken to mean, in particular with regard to the properties of particles, particularly particles in the first examination medium. The properties are in particular properties, such as the size of the particles which occur in the first examination medium. Further properties to be considered for a particle can be the number, length, surface area and the volume of the particle. Furthermore, the color of the examination medium can also be taken into account, in particular with the particles it contains, with regard to light refraction, diffraction and absorption.

Here, the behavior of the examination object can be considered in particular with regard to an examination medium flowing through it. Here, in particular the separating influence of the examination object, such as the system, on the examination medium flowing through it is considered. Thus, the examination medium is considered before and after it passes through the examination object. Here, the selected approach is based on a mechanical procedure and the reproducibility of the approach is very high. At this point the method does not take into account any microbiological standards for the assessment of a hygiene status, which however, provided they are available, could be included in this method.

The first examination medium can comprise typically a first fluid. In this respect the first fluid can comprise, for example, a liquid foodstuff. The first fluid can therefore comprise water. Typically, the first examination medium can comprise a solid, and in particular a mixture, such as a suspension of the first fluid and the solid. Typically, the solid comprises small particles, which are suspended in the suspension provided it is stirred, and which slowly form a deposit when the suspension is stationary.

With regard to the use of filling systems for foodstuffs, in particular juices or liquids to which additives are added, the particles can comprise solids of this nature, which are contained in foodstuffs, for example fruit pulp, or which are added to the foodstuff. Similarly, the particles can comprise sandy particles, in particular silica sand. Consequently, it is also possible, to assess say a flash pasteurization system for milk products with regard to its hygiene status in that the equipment has a silica sand/milk suspension passed through it.

In the method according to the disclosure, as described above, the property distribution of the first examination medium can comprise in particular the particle size distribution and/or the change in the particle size distribution before and after passage through the examination object.

Furthermore, in addition to measuring the property distribution of the first examination medium, the method according to the disclosure can consider the change in mass, in particular with regard to the percentage loss of mass or increase in mass. Here it is self-evident that a suitable test volume, for example, a liter (1 l) or a large volume unit can be considered before and after the passage of the examination medium through the examination object. Furthermore, it is self-evident that in the method outlined above the influence of a flow velocity of the examination medium through the examination object should be kept as low as possible. This means that the examination medium should, for example, only be pumped through the system at a weak pressure. The pump speed here should typically not be changed until a measurement has been obtained.

The method according to the disclosure can furthermore comprise the determination of the cleaning property of the examination object after the determination of the degree of contamination as described above with the examination object filled with the first examination medium. After the determination of the degree of contamination the examination object is generally filled with the first examination medium. Thus, typically before the start of the determination of the cleaning property a property distribution of the first examination medium, which has been passed through the examination object, is known. At least, the examination object is typically filled with the first examination medium before the determination of the cleaning property. In the following, the method typically comprises the step of measuring a property distribution of a second examination medium before and after the passage through the examination object and comparison of the property distribution of the second examination medium after passage through the examination object with the property distribution before passage through the examination object and with the property distribution of the first medium. Here, the second examination medium can comprise a second fluid, whereby in particular the second fluid corresponds to the first fluid, thus for example, for the first and the second examination medium water or milk can be used as the fluid or a different foodstuff. Here, the second examination medium generally contains no particles, such as sand, as described above, before being introduced/passing through the examination object. During the passage through the examination object the second examination medium, generally the second fluid, can take up particles. Following the method according to the disclosure, the property distribution of the second examination medium can comprise the determination of the particle size distribution and/or the change in the particle size distribution before and after the passage.

During the measurement of the property distribution of the second examination medium the change in mass, in particular the percentage loss of mass or gain in mass can be determined here with regard to the second examination medium. Here the situation is that the second examination medium typically takes up particles on passing through the examination object. These particles typically originate from the determination of the degree of contamination following the method according to the disclosure as described above.

The measurement of the property distribution, in particular the particle size distribution, can take place by means of a laser diffraction spectrometer. Here, using a laser directed at the sample and with the interference pattern produced in this way, the particle size distribution before and after passage through the examination object can be measured. Furthermore, the detection of the change of mass can take place, for example, at least at the beginning and the end of the respective measurement process. In this way it is known for example, how large the loss of mass, that is the change of mass, during the determination of the degree of contamination can be with regard to the first examination medium. Accordingly it can be considered by how far the second examination medium can take up particles by passing through the contaminated examination object and indicate these particles as a change in mass after passage of the second examination medium.

Furthermore, the disclosure, as described above, can comprise a device for carrying out the method as described above. This device can comprise an intake container and an output container. These containers can, for example, be separated by the examination object. Furthermore, the device can comprise a suitable conveying or transport device, in particular pipes, for extracting the first and/or the second examination medium from the intake container and for passing the first or the second examination medium through the examination object. Furthermore, the conveying device can be formed to output the examination media after passage through the examination object and to retain them in an output container. In the output container a detection device, in particular a laser diffraction spectrometer, can be formed for the determination of the property distribution of the first or the second examination medium. It is self-evident that also other suitable optical devices can be provided in the device which determine the property distribution of the examination media. Furthermore, the intake and/or output container can be provided with a homogenizing device, in particular a stirrer, to mix the mixture of fluid and particles appropriately before and after the passage through the system. Here it is clear that the homogenizing acts against the sedimentation in the intake and/or output containers, so that sedimentation appears to be only possible within the examination object. Furthermore, additional measuring devices can be provided in the device for the measurement of temperature, pressure, particle sizes of particles or other property distributions in the intake and/or output containers and in the examination object itself, if spectroscopic data are also required during the passage through the examination object. Furthermore, the device according to the disclosure can be provided with a measurement system, which employs laser diffraction spectroscopy for the determination of the particle size distribution and for the determination of mass.

The disclosure is explained exemplarily in the following based on the drawing, wherein the following are shown.

DETAILED DESCRIPTION OF THE PREFERRED EMBODIMENT

By way of illustration, in the following the example of an ideal and a real hygiene-compatible pipe system is described.

An ideal pipe, i.e. a pipe which is essentially straight, has self-draining, polished internal surfaces without gaps and ridges and has no dead spaces or additional connection points, is to be examined by a sand/water suspension according to the disclosure. A pipe of this nature ideally does not affect the composition of the sand/water suspension at any point in time. Accordingly, the particle size distribution at any point in time and at any place is constant taking into account the type of flow in the pipe, as well as the pressure and temperature. This means that essentially the total mass of the particles which are taken in is also retained at the end of the pipe after they have passed through the pipe. Thus, the mechanical contamination tendency of this system is very low, ideally even zero, and the pipe therefore cannot be contaminated.

Figure 1A:
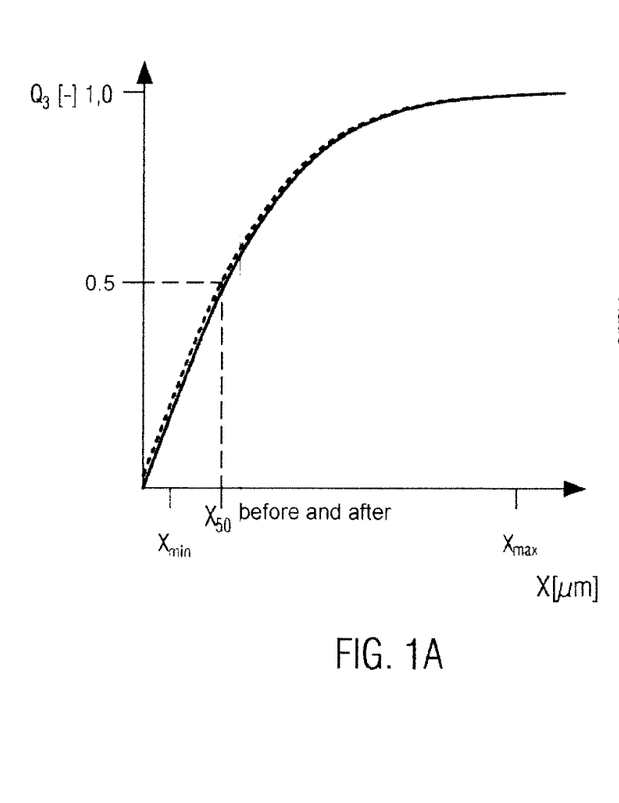
FIG. 1A Summary of particle size distribution for an ideal pipe.
Figure 1B:
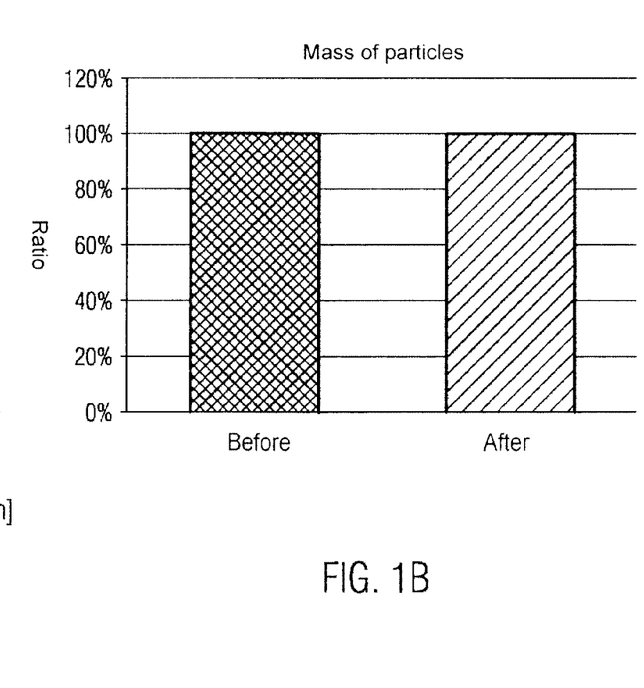
FIG. 1B Summary of change of mass for an ideal pipe.

FIGS. 1 and 1A illustrate the examination of a pipe of this nature. FIG. 1A illustrates the particle size distribution before passage of the sand/water suspension through the pipe as a dotted line and the particle size distribution after passage of the sand/water suspension through the pipe. FIG. 1B furthermore illustrates the change in mass.

FIG. 1A on the ordinate D shows the minimum diameter, that is the diameter of the particles $x_{min}$, measured in the suspension, i.e. the sand/water mixture. Furthermore, the abscissa shows the corresponding maximum diameter of the examined particles of the suspension $x_{max}$. Here, x may be between $x_{min}$ and $x_{max}$ and typically has the order of magnitude of a few micrometers. Furthermore the $x_{50}$ value is indicated. This is the median, i.e. half of all particles referred to a certain quantity type is greater or less than this value. The quantity $Q_3$ is entered on the ordinate of FIG. 1A. Here, this is the distribution sum $Q_r(x_i)$, where r=3, which relates to the volume, respectively the mass. Here, $Q_3(x_i)$ for a given diameter $x_i$ is supplied by $$Q_3(x_i) = \frac{\text{Quantity\_of\_all\_particles\_with\_x} \leq x_i}{\text{Total\_quantity\_of\_all\_particles}}$$

In FIG. 1A the dotted and the dashed curves lie one above the other. The representation shows therefore that all particles of any size which enter the pipe also leave it again. The composition at the illustrated points in time "Before" and "After" is not changed by this. The $x_{50}$ value is unchanged. Accordingly, FIG. 1B illustrates the change in mass due to the ideal pipe under consideration. In this fictitious example the change in mass is the same before and after passage through the ideal pipe. This means that no change of mass took place and 100% of the particles under consideration has been passed out of the pipe again. Here too, attention must be given to appropriately suitable standardization to a test volume, e.g. 1 liter or a greater or smaller volume.

Figure 2A:
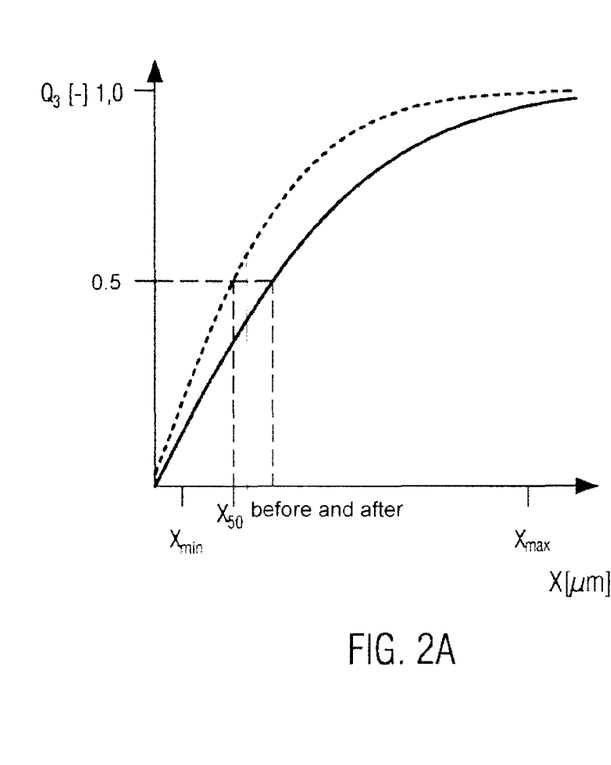
FIG. 2A Particle size distribution for a real pipe.
Figure 2B:
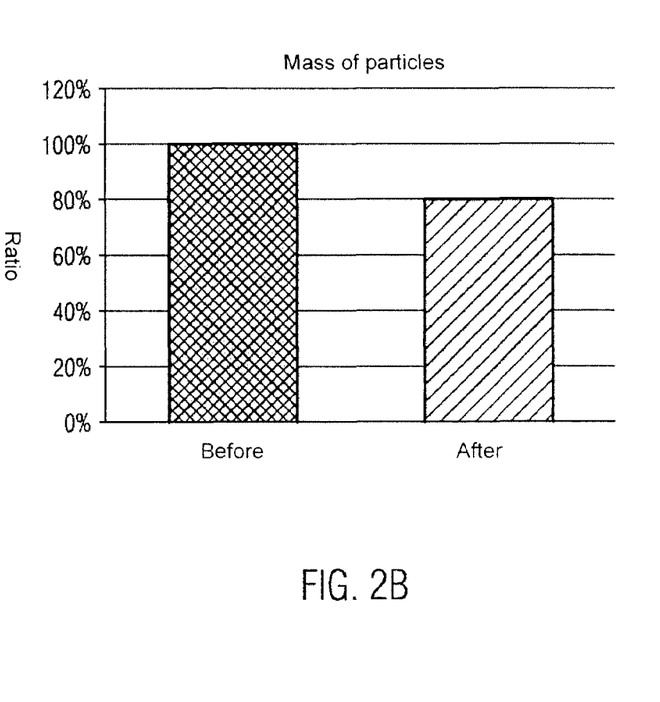
FIG. 2B Change of mass for a real pipe.

Furthermore, a pipe will now be considered which is not ideal, but real. A pipe of this nature can for example be bent and in particular comprise internally a rough surface with gaps and dead spaces or even connection points for further pipes. Accordingly, the suspension composition during the passage of the silica sand suspension is affected at each point in time. Separation of individual particle sizes can occur, so that the particle size distribution can vary over the period of the test. If the test is of adequately long duration, then the maximum contamination of the system, i.e. the degree of contamination, is reached when the particle size distribution of the suspension passing through no longer changes. This can also be designated as validation of the contamination tendency or as a reference point for the contamination tendency. The total mass of particles provided at the intake is not obtained at the output. Accordingly, FIG. 2 illustrates a difference between the changes of mass before and after the passage of the suspension through the real pipe. Similarly, FIG. 2A shows a displacement of the dotted line compared to the dashed line and a change in the corresponding $x_{50}$ value. FIGS. 2A and 2B otherwise show the same quantities as the corresponding FIGS. 1A and 1B. The $x_{50}$ value is increased in FIG. 2A. From this it can be seen that many, in particular small, particles remain in the system. The total mass of particles reduces accordingly.

As a further step, the determination of the cleaning property of the pipe under consideration is discussed. Since a sand/water suspension was passed through both pipes, water is now passed through the system, i.e. the pipe, to determine the cleaning property. With the exit of the liquid, i.e. the water, which has now taken up any particles remaining in the pipes, the particle size distribution is detected again and the total mass of particles acquired. If no more changes occur or all particles are again obtained at the output, the system is regarded as cleaned. This can be designated as "validation of the system cleanability". The change in the particle size distribution, whereby the $Q_3$ distribution has been used as an example—although it is possible to use a different quantity type or to convert to a quantity type—describes the cleaning property of the system under consideration, here the given real pipe. If small particles remain in the system and the $x_{50}$ value increases accordingly, referred to an equivalence factor to be appropriately defined, this may be explained by the presence of many small gaps. If however the $x_{50}$ value hardly changes and despite this it is not possible to again obtain the mass of particles out of the test system, then this may imply that large and small gaps are present by which both small and also large particles are selectively retained.

The appropriately presented method according to the disclosure enables the hygiene status of the system to be assessed. There is even the possibility of comparing two systems. The outlined ideal pipe can be regarded as the optimum and therefore as a reference value. Referred to this standard, it can be used to compare and classify other pipes. An appropriate standardization can be transferred to other system parts or complete systems. This means that quantifiable statements can be made, such as—purely fictitious and exemplary—the statement that "an examined pipe for example is five times as easy to contaminate as the reference pipe".

The same applies to cleaning. The disclosure provides the advantage that also more complex systems, in particular pipework as well as complete machines, can be assessed in this manner. It is even possible to change from the flow medium of water to another liquid foodstuff. Here it is important that the complete particle collective is always considered. A different suspension medium causes a different interaction and can cause changes in the corresponding test result, which can however again be appropriately referenced and standardized.

Figure 3:
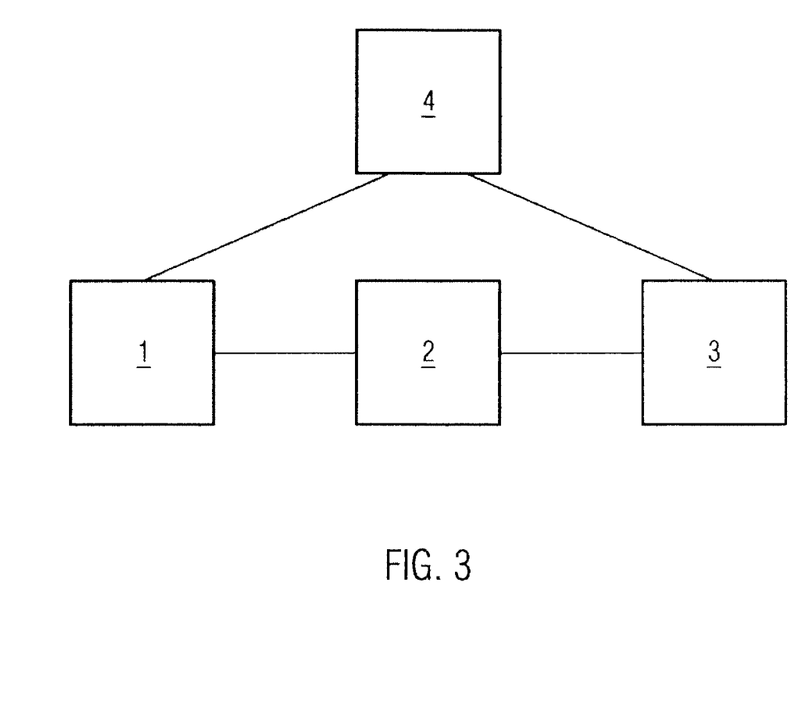
FIG. 3 Schematic sketch of a device according to the disclosure.

The above described ideas for the determination of the degree of contamination of the ideal pipe and of a real pipe and correspondingly of a degree of cleaning of an ideal pipe have been presented and discussed in the FIGS. 1A, 1B, 2A and 2B. According to the figures, standards for validation can be defined. FIG. 3 illustrates the implementation of the basic schematic diagram for the discontinuous and/or continuous method of considering the degree of contamination and the cleaning property of the system with a corresponding device. FIG. 3 illustrates an intake container 1, an output container 3 and an examination object 2. These are typically installed in series. The intake and output containers 1 and 3 can for example be installed separately from the examination object 2. Suitable pipes are used to connect these containers to the examination object 2. An examination medium, for example a sand/water suspension, is passed or pumped out of the intake container 1 through the examination object 2. Then the examination medium, i.e. the suspension, is passed into the output container 3. At defined time intervals the particle size distribution of the suspension is determined by means of a detection device 4. At least at the beginning and at the end of the process the mass of the supplied and of the returned particles, for example sand, is measured by the detection device 4.

Here the determination of the particle sizes and therefore of the particle size distribution can take place in continuous form.

Figure 4:
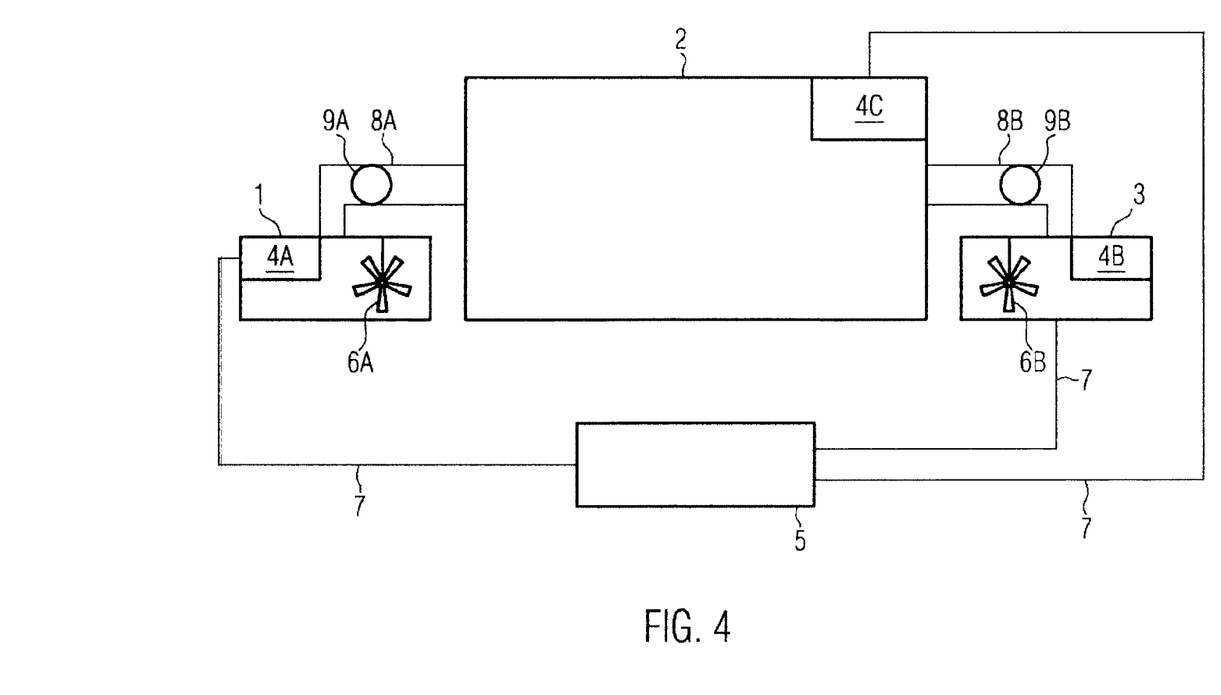
FIG. 4 An embodiment of a device according to the disclosure.

FIG. 4 illustrates an embodiment according to the present disclosure. FIG. 4 illustrates in particular an intake container 1, an output container 3 and an examination object 2. FIG. 4 shows that the intake container 1 and the output container 3 are respectively connected through the pipes 8a and 8b to the examination object 2. The examination object 2 can be a system for the treatment or filling of liquid foodstuffs. The pipes 8a and 8b can be assigned to pumps 9a and 9b, which pass an examination medium from the intake container 1 into the examination object 2 and from the examination object 2 into the output container 3. Here, the pumping speed of the pumps 9a and 9b is typically constant and low. The intake container 1 and the output container 3 also comprise respectively devices 6a and 6b, in particular stirrers, for homogenizing the examination medium present in the respective containers. The stirrers 6a and 6b can therefore prevent sedimentation of particles in the suspension present in the intake/output containers. FIG. 4 also illustrates a control unit 5, say a CPU or a computer, which is connected through control lines 7 to control and/or measurement devices 4a and 4b in the intake container 1 and output container 3 respectively. In this way, the particles in the suspensions in the intake container 1 and output container 3 can be determined with, for example, two measurement systems 4a and 4b, which can comprise laser diffraction spectrometers. Thus, the particle size distribution of the particles can be determined. Furthermore, FIG. 4 illustrates optionally also a measurement unit 4c, where it is desired to obtain data about the particle size distribution of the passed suspension also within the examination object 2. An approach of this nature is particularly feasible for larger systems. Similarly, it may be possible (not illustrated here), that with regard to a discontinuous form of the sample extraction only one measurement unit 4b needs to be present in the output container 3. The measurement step can thus take place independently of the passage of the suspension through the examination object and in particular after the passage through the examination object. Here it is particularly advantageous if the stirrer 6b homogenizes the suspension retained in the output container 3.

Figure 5:
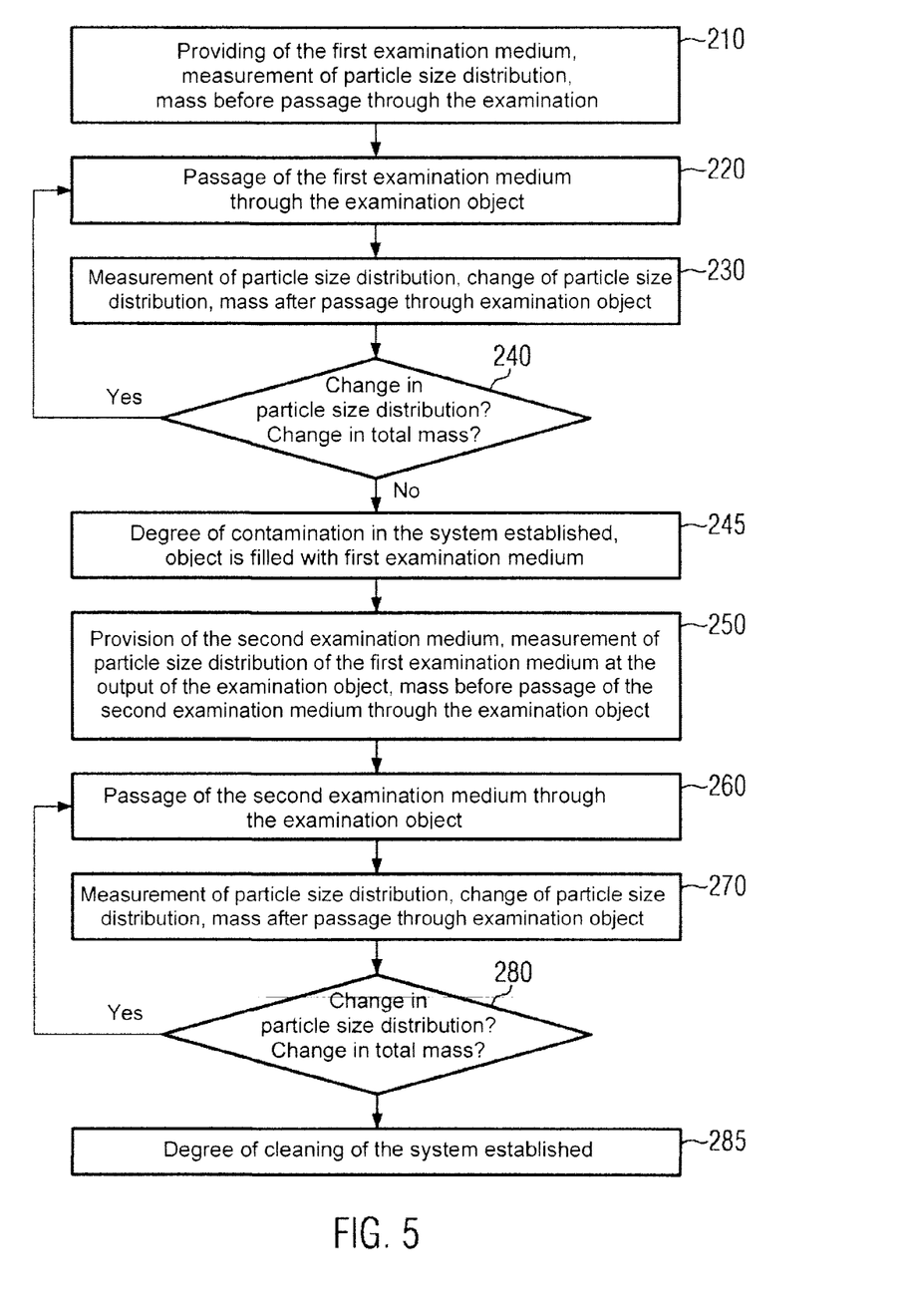
FIG. 5 Sketch of the method according to the disclosure.

FIG. 5 illustrates an example of a method according to the present disclosure. In step 210 a first examination medium, say a suspension of sand and water, is made available as well as the measurement of a property distribution, such as a particle size distribution, before the passage through the examination object. According to FIG. 4 a measurement of this nature can take place for example in the output container. In step 220 the passage of the first examination medium through the examination object occurs. In step 230 the measurement of a particle size distribution occurs, as well as the change in the particle size distribution compared to the particle size distribution measured in step 210 and also the consideration of the total mass after the passage through the examination object. In step 240 an examination is made of whether a change in the particle size distribution has occurred compared to the first measurement step. If this is the case, the passage of the first examination medium is continued according to step 220. Here, it is self-evident that in each case the last value of the particle size distribution and the total mass are considered when step 240 has again been reached. When no further changes occur in step 240, step 245 follows in which the degree of contamination of the system is considered as "determined".

Based on the preceding steps 210-240, in step 245 the object is filled with the examination medium, i.e. the first examination medium. If the explicit measurement steps of the preceding steps 210-240 are not to be carried out, then at least it should be ensured that the examination object is filled with the first examination medium, say a sand/water suspension. In step 250 a second examination medium is made available. Typically, the second examination medium is the fluid of the first examination medium without the particles of the suspension of the first examination medium. The particle size distribution of the first examination medium at the output of the examination object is measured at the beginning of step 250 and forms a reference value. The mass is measured as a reference value before the passage of the second examination medium. In step 260 the second examination medium is passed through the examination object. In step 270 the particle size distribution and the change in the particle size distribution are determined after the passage of the second examination medium through the examination object. In step 280 an examination is made of whether a change in the particle size distribution or a change in the total mass has occurred. If this is observed, the passage of the second examination medium through the examination object is continued. Here, the values measured in step 270 or 280 are taken as the new reference values. If the method converges and changes in the particle size distribution or in the total mass are no longer found, the method has converged and in step 285 the degree of cleaning of the system is considered as "determined". With that, the method terminates.

The following can therefore be established: the present disclosure is based on the consideration of an apparatus or a pipe as the separation device with regard to a particle suspension. Accordingly, a dependable assessment of the hygiene status of the system is made available. A control instrument for the assessment of the contamination and cleaning properties of a system can be made available. Through tests on a system, for example on a flash pasteurization system for milk products, a statement can be made of how difficult or easy it is to contaminate the system. Accordingly, statements about the service periods can be made; a cleaning program can be formulated based on this. Accordingly, a described detection device with optical signals for beverage suspensions can be made available. The principle for this can be the detection of the change in the particle size distribution of a certain substance present in the product, for example fibres or fruit constituents in a juice.

Summarizing, it can be said that previously there was no microbiological standard for the assessment of hygiene status. A standard of this nature, providing it exists, can be integrated into the appropriate method. The appropriate mechanical procedural method is robust and has high reproducibility. Operation, in particular with a sand/water suspension, particularly silica sand/water, is recommended, because silica sand and water do not react with one another. Furthermore, a suspension of this nature is temperature-resistant. It can be easily stored. The suspended silica particles can be easily separated from organic particles. And the suspension is not subject to reaction with micro-organisms. A suspension of this nature furthermore presents no danger to people and machines and due to the high availability of both constituents, a suspension of this nature can be manufactured very economically. The corresponding results from the system are almost immediately available after testing the system and there is no outlay for incubation or analysis times. The outlay for the apparatus of this nature is low and facilitates the comparison of different systems and different products together in systems.

It is self-evident that the features mentioned in the above described embodiments are not restricted particularly to the combinations illustrated in the figures, but rather are also possible in other combinations.

The invention claimed is:

1. A method for determining a degree of contamination of an examination object, comprising:
   determining the degree of contamination of the examination object by measuring a property distribution of a first examination medium before and after passage of the first examination medium through the examination object;
   determining a cleaning property of the examination object by measuring a property distribution of a second examination medium before and after passage of the second examination medium through the examination object; and
   comparing the property distribution of the second examination medium after passage through the examination object with the property distribution of the first examination medium after the passage through the examination object,
   wherein the first examination medium includes a suspension of a first liquid and a solid.

2. The method according to claim 1, wherein the first liquid comprises:
   a liquid foodstuff.

3. The method according to claim 1, wherein the first liquid comprises: water.

4. The method according to claim 1, wherein the solid comprises particles including one or more of:
   particles contained in the foodstuff; and
   particles added to the foodstuff.

5. The method according to claim 1, wherein the particles comprise sandy particles.

6. The method according claim 5, wherein the sandy particles comprise silica sand.

7. The method according to claim 1, wherein the property distribution of the first examination medium comprises one of:
   a particle size distribution,
      a change in the particle size distribution before and after passage of the first examination medium through the examination object; and
   a combination of the particle size distribution and the change in the particle size distribution.

8. The method according to claim 1, further comprising:
   determining a change in mass during the measurement of the property distribution of the first examination medium before and after passage of the first examination medium through the examination object.

9. The method according claim 8, wherein the change in mass comprises the percentage loss or gain in mass.

10. The method according to claim 1, wherein the second examination medium comprises:
    a second liquid.

11. The method according to claim 10, wherein the second liquid is the same as the first liquid.

12. The method according to claim 1, wherein the property distribution of the second examination medium comprises one or more of:
    a particle size distribution;
    a change in a particle size distribution before and after passage of the second examination medium through the examination object; and
    a combination of the particle size distribution and the change in the particle size distribution.

13. The method according to claim 12, further comprising:
    determining a change in mass of the second examination medium through the examination object due to passage of the second examination medium through the examination object.

14. The method according to claim 13, wherein detection of the change in mass takes place at least at a beginning and an end of the measurement of the property distribution of the second examination medium through the examination object.

15. The method according claim 13, wherein the change in mass comprises the percentage loss or gain in mass.

16. The method according to claim 12, wherein the measurement of one of the particle size distribution, the change in the particle size distribution, and a combination thereof is performed at one of:
    predefined time intervals; and
    continuously.

17. The method according to claim 1, wherein the measurement is performed using a laser diffraction spectrometer.

18. The method according claim 1, wherein the system comprises a system for filling liquid foodstuffs.

19. The method according claim 1, wherein the component or subsection of a system comprises a pipe.

20. A device for determining a degree of contamination of an examination object, comprising:
- a conveying device configured to remove a first and a second examination medium from an intake container and to pass the first and the second examination medium through an examination object and into an output container; and
- a detection device configured to:
    - determine a property distribution of the first examination medium by measuring a property distribution of the first examination medium before and after passage of the first examination medium through the examination object;
    - determine a cleaning property of the examination object by measuring a property distribution of a second examination medium before and after passage of the second examination medium through the examination object; and
    - compare the property distribution of the second examination medium after passage through the examination object with the property distribution of the first examination medium after the passage through the examination object to determine the degree of contamination of the examination object,
    - wherein the first examination medium includes a suspension of a first liquid and a solid, and
    - wherein the second examination medium includes a second liquid.

21. The device according to claim 20, wherein one or more of the intake container and the output container include a homogenizing device configured to mix the suspension.

22. The device according to claim 20, further comprising:
a measurement device configured to measure one or more of:
temperature of the first or the second examination medium;
pressure of the first or the second examination medium;
a change in mass of the first or the second examination medium from passage through the examination object;
particle sizes of particles in the first examination medium; and
a property distribution of the first or the second examination medium while the first or the second examination device is in the intake container, the output container, or the examination object.

23. The device according to claim 20, further comprising:
a measurement system configured to utilize laser diffraction spectroscopy for the determination of the particle size distributions and for the determination of change in mass.

24. The device according claim 20, wherein the solid comprises particles.

* * * * *